United States Patent
Franchi

[11] Patent Number: 6,050,932
[45] Date of Patent: Apr. 18, 2000

[54] CONTROL CIRCUIT FOR AN IMPLANTABLE HEART-ASSIST PUMP OF THE BACK-PRESSURE BALLOON TYPE

[75] Inventor: Pierre Franchi, Vitry-sur-Seine, France

[73] Assignee: Synthelabo Biomedical ( Societe Anonyme), Le Plessis-Robinson, France

[21] Appl. No.: 09/125,650
[22] PCT Filed: Feb. 19, 1997
[86] PCT No.: PCT/FR97/00302
  § 371 Date: Dec. 11, 1998
  § 102(e) Date: Dec. 11, 1998
[87] PCT Pub. No.: WO97/30739
  PCT Pub. Date: Aug. 28, 1997

[30] Foreign Application Priority Data

Feb. 21, 1996 [FR] France .................................. 96 02135

[51] Int. Cl.⁷ .................................................. A61M 1/12
[52] U.S. Cl. .................................................. 600/16
[58] Field of Search ........................................ 600/16, 18

[56] References Cited

U.S. PATENT DOCUMENTS 3,698,381 10/1972 Federico et al. ........................... 600/18

Primary Examiner—William E. Kamm
Attorney, Agent, or Firm—Jacobson, Price, Holman & Stern, PLLC

[57] ABSTRACT

The pump (10) has variable volume means (24) co-operating with a distinct volume (20) through which the blood flows for the purpose of varying said volume (20) through which the blood flows in cyclical and controlled manner. According to the invention, the control circuit for the pump comprises: means for sensing data representative of aortic pressure (P(t)); means for sensing data representative of venous oxygen concentration ($PO_{2V}$); means for sensing data representative of aortic oxygen concentration ($PO_{2A}$); means for sensing data representative of heartbeat frequency (F); and/or means for sensing data representative of the myocardial contractility (dP/dt). The circuit can control the rates (u(t), v(t)) at which said volume varies during the systolic and diastolic phases of the myocardium, and also the instants ($t_A$; $t_R$) at which said variation of the volume starts during the systolic and diastolic phases.

12 Claims, 1 Drawing Sheet

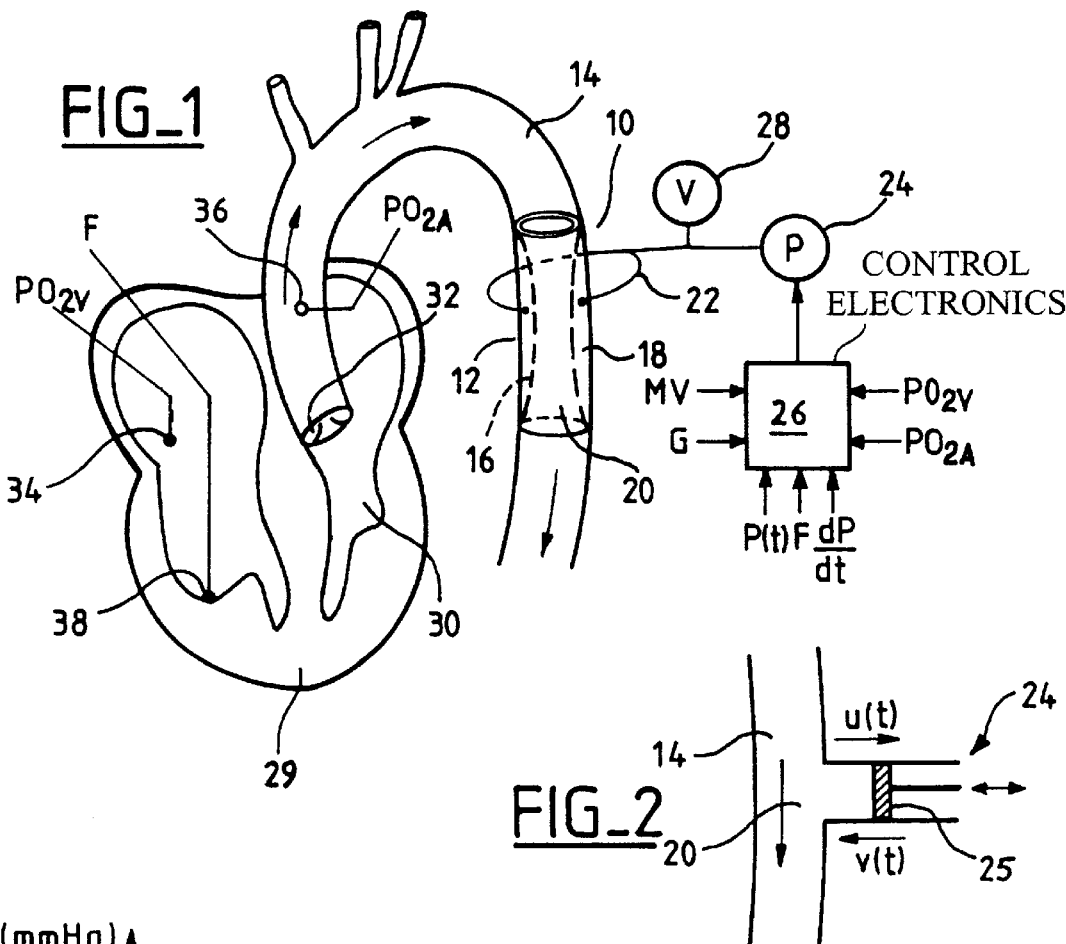
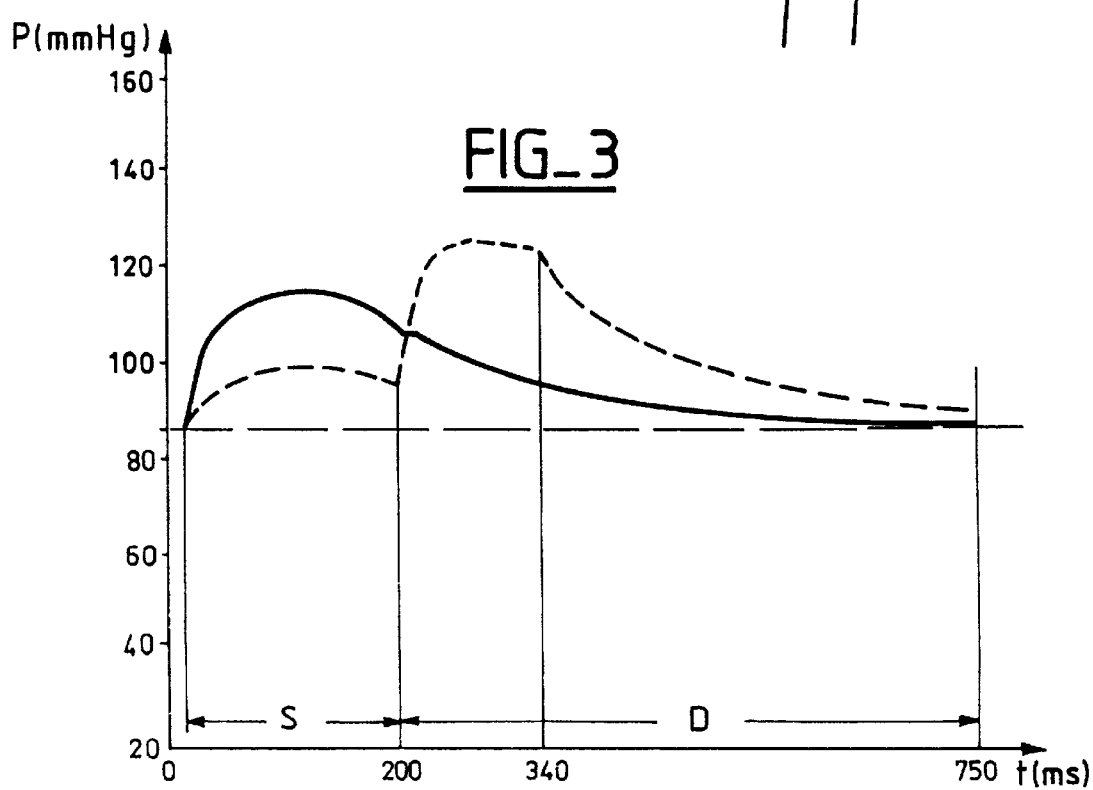

CONTROL CIRCUIT FOR AN IMPLANTABLE HEART-ASSIST PUMP OF THE BACK-PRESSURE BALLOON TYPE

The invention relates to a control circuit for an implantable heart-assist pump of the back-pressure balloon type. The technique using an intra-aortic back-pressure balloon is well known for providing effective hemodynamic assistance to the left ventricle in the event of congestive heart failure: the balloon is inserted in the down branch of the aorta and is inflated during the diastolic phase of the heart cycle, and as a result injects an additional volume of blood into the network of arteries both upstream and downstream from its position. Deflated during the following heart systole, it decreases the load on the left ventricle thus enabling blood flow rate to be increased. The hemodynamic balance is positive: an increase in the injection fraction; a decrease in the telediastolic pressure. Thus, the balloon delivers additional energy which the ventricle is not able to supply, and the state of the patient is very significantly improved.

Implanted systems have already been proposed which make it possible to implement that technique in an entirely self-contained manner, for example as described in U.S. Pat. No. 5,222,980, or indeed in French application 96/00949 filed on Jan. 26, 1996 belonging to the same proprietor as the present application and entitled *Pompe d'assistance cardiaque implantable du type à ballonnet de contrepression* [An implantable heart-assist pump of the back-pressure balloon type].

Both of those documents describe a permanent implantable heart-assist pump inserted in the descending aorta, operating on the above-mentioned principle of a back-pressure balloon constituted by a flexible and elastic membrane in the form of a sleeve whose axis coincides with that of the aorta and which is put in the place of a segment of aorta that has been removed. The membrane is contained in a rigid chamber having substantially the same shape as the membrane at rest, and into which a hydraulic fluid is injected from an external generator, thereby compressing the membrane and thus reducing the volume of blood that it contains. Conversely, extracting the hydraulic fluid causes the inside volume of the membrane to increase, and thus the pump to be filled.

More precisely, an object of the present invention is to provide a control circuit for such an implantable heart-assist pump which controls the appliance so that its behaviour is as physiological as possible, i.e. it mitigates the heart failure without requiring excessive or antinatural effort from the weakened myocardium, and which, throughout the cardiovascular system, generates blood flow having characteristics, in particular pressure wave, that are as close to possible to those of a healthy organism.

Another object of the invention is to provide variable control of the pump that is adapted to the real hemodynamic demand of the patient, firstly to limit he energy consumption of the implanted appliance, and secondly, and above all, to disturb the natural hemeostatic equilibrium as little as possible, thus avoiding possible organic complications in the long term following implantation of the pump.

To this end, the invention provides a circuit for controlling an implantable heart-assist pump of the back-pressure balloon type of the above-specified type, i.e. comprising variable volume means co-operating with a separate volume through which blood flows for the purpose of modifying said volume through which blood flows cyclically and in controlled manner, the circuit being characterized in that it includes at least some of the means in the group comprising:

means for sensing data representative of aortic pressure; means for sensing data representative of venous oxygen concentration; means for sensing data representative of aortic oxygen concentration; means for sensing data representative of heartbeat frequency; and means for sensing data representative of the myocardial contractility.

According to a certain number of advantageous characteristics:

the circuit includes heart-assist control means for controlling the variable volume means, said control means including at least some of the means in the group comprising: means for controlling the rate of variation of said volume during the systolic phase of the myocardium; means for controlling the rate of variation of said volume during the diastolic phase of the myocardium; means for controlling the instant at which said volume variation starts during the systolic phase; and means for controlling the instant at which said volume variation starts during the diastolic phase;

in a first embodiment, the assistance given to the heart may be predetermined, operating on the basis of: (i) a programmed set of rest values for reference parameters, said parameters comprising at least one of the following parameters: the rate at which the volume varies during the systolic phase of the myocardium; the rate at which the volume varies during the diastolic phase of the myocardium; the instant at which said volume variation during the systolic phase begins; and the instant at which said volume variation during the diastolic phase beings; and (ii) an algorithm for correcting at least one of said parameters as a function of the heartbeat frequency;

the circuit further includes means for sensing data representative of the metabolic needs and/or the physical activity of the patient; and in a second embodiment, the assistance given to the heart may be automatic, operating on the basis of: (i) a sensed representative data set generated in real time comprising at least: aortic pressure; venous oxygen concentration; aortic oxygen concentration; heartbeat frequency; and myocardial contractility; (ii) a corresponding set of reference parameters; (iii) differences determined between said representative data set and said reference set; and (iv) an algorithm for implementing variable volume means as a function of the differences determined in this way. In which case, advantageously, the algorithm for implementing variable volume means serves to track heart assistance, particularly by applying the assistance by successive approximations; in addition, the heart assistance may serve to correct the data set generated in real time or the reference set.

Other characteristics of the invention appear on reading the following description of an embodiment of the invention.

FIG. 1 is a diagrammatic view showing the pump of the invention, its control circuit, and the environment in which the appliance as a whole is implanted.

FIG. 2 shows how operation of the FIG. 1 pump is modelled.

FIG. 3 shows the characteristic of the pressure wave as a function of time over one heart cycle, with and without assistance by the pump of the invention.

In FIG. 1, there is shown an implantable heart-assist pump of a type that is itself known (e.g. from above-mentioned U.S. Pat. No. 5,222,980 or from French application 96/00949), in which the main element 10 comprises a rigid body 12, typically in the form of a circular cylinder, open at both ends and inserted in the descending aorta 14, the axis of the aorta and the axis of the body 12 coinciding, and with both of these two elements having substantially the same diameter.

The rigid body 12 contains a flexible membrane 16. In the embodiment shown, the membrane 16 at rest is similar in shape to the body 12, so as to be substantially a close fit therein, and it is secured thereto at both ends over its entire periphery.

Between the body 12 and the membrane 16, there is thus defined a closed intermediate space 18 of variable volume, and inside the membrane 16 there is defined a central space 20, also of variable volume, with this volume decreasing when the volume 18 is increased, and vice versa.

The volume of the space 18 is increased by injecting a hydraulic fluid (typically a biocompatible aqueous saline solution, e.g. a physiological serum) via one or preferably more points connected via a duct 22 to a variable pressure source 24 controlled by control electronics 26. Advantageously, a hydraulic fluid reservoir 28 may also be provided in the form of a septum that is accessible percutaneously by means of a hypodermic needle to enable the volume and/or the salinity of the fluid to be adjusted, or to enable it to be emptied out.

The invention relates more particularly to the circuit 26 which controls the pressure source 24.

As shown in FIG. 2, the pump can be modelled in the form of a piston 25 whose displacement in one direction or the other gives rise to a change in the volume 20 of the aorta. This artificial variation of the volume 20 in the aorta 14 is comparable to the natural dilatation of a healthy artery as the result of the elasticity of the walls of the artery, and is of greater amplitude.

More precisely, during heart systole, contraction of the myocardium 29 causes, in succession: the pressure to rise in the left ventricle 30; the aortic valve 32 to open; and blood to be ejected into the aorta 14. Heart beats are such that systole is of perceptibly shorter duration than the heart cycle, thereby increasing the speed of systolic ejection. The elasticity of the arteries avoids the need for a corresponding excess demand for power from the ventricle to overcome the load provided by the inertia and the resistance of the column of blood that it is to put into motion, and thus makes it possible, so to speak, to deliver energy at a lower instantaneous rate during diastole.

Heart failure is characterized by the incapacity of the ventricle to deliver the quantity of blood required by the organism because it does not have the necessary power, and this may or may not be accompanied by hardening of the arteries (although hardening of the arteries aggravates this pathological condition very greatly).

Under such circumstances, the heart-assist pump performs two functions: firstly it provides additional elasticity in artificial manner to the aorta, as described above, giving the same benefit as that provided by the natural elasticity of the arterial network; secondly, and in accordance with an original aspect of the invention, the pump can delivery additional energy to the circulation system during diastole.

Considering the model shown in FIG. 2, the total volume produced artificially by displacing the piston 25 in the heart-assist pump at the end of displacement is given by:

$$\Sigma \cdot \int_S u(t) dt$$

where $\Sigma$ is the surface area of the piston and $u(t)$ is the speed of displacement of the piston which varies as a function of time throughout all or part of systole S.

This volume of blood which is stored in the pump during systole is subsequently reinjected into the aorta during the diastole D following the systole, by the piston moving in the opposite direction at speed $v(t)$, which is likewise variable as a function of time during all or part of diastole D (where the speed $v(t)$ is independent of $u(t)$).

From an energy point of view, during systole the pump takes energy $E_i$:

$$E_i = \Sigma \cdot \int_S P(t) \cdot u(t) dt$$

$P(t)$ being the pressure exerted by the blood on the piston.

During diastole, the pump restores energy $E_o$:

$$E_o = \Sigma \cdot \int_D P(t) \cdot v(t) dt$$

The energy balance $E_o - E_i$ due to the prosthesis can be:

negative, which means that the heart is delivering energy to the prosthesis (this possibility is clearly not advantageous);

zero or slightly positive: the pump then behaves essentially as additional elastance (elasticity factor), that combines with the natural elastance of the artery in the operating scheme described above and providing the same benefit. Under such circumstances, the heart provides all of the energy that is required. This can apply, for example, to a patient who is resting; and positive, in which case the assistance given to the heart is taken further, the substantial increase in the volume of blood stored by the pump and the corresponding decrease in the systolic pressure making it possible significantly to increase the systolic ejection volume using energy from the heart that is less than or equal to that which it provided before the increase. In addition to its function of providing additional elastance, the pump acts during diastole to provide the extra energy required to compensate for the heart deficit.

In this way, by modulating the volume stored and the energy delivered by the pump, it is possible to deliver assistance to the heart on a cycle-by-cycle basis in "doses" as a function of the hemodynamic demand. The doctor can organize this "dosage" so as to load the heart to the maximum of its operating capacity under all circumstances, or to only a fraction thereof, by means of adjustments and of automatic responses as described below.

The major advantage of proportional dosage of this type is to minimize the energy consumption of the appliance.

It is also possible to limit the action of the machine on the circulation system so as to disturb the natural homeostatic equilibrium as little as possible, thereby avoiding severe repercussions in the long term on major organic functions, such as the renal and hepatic functions.

Finally, it can be expected that this method of providing assistance that is adaptive and limited encourages rehabilitation of the heart.

Such heart assistance is implemented by the circuit of the invention which operates as follows.

DATA

Firstly, the state of the cardiovascular system is characterized by data which is made accessible to the appliance by sensors. The data used is as follows:

aortic pressure as a function of time P(t);

venous oxygen concentration $PO_{2V}$;

aortic oxygen concentration $PO_{2A}$;

heartbeat frequency F; and myocardial contractility dP/dt.

This list not limiting, thus, minute volume MV and/or posture and/or still further parameters can also be taken into account from appropriate corresponding sensors (e.g. from accelerometers for posture and activity G).

DATA ACQUISITION

The data is obtained as follows:

P(t): by a specific sensor disposed in the pump on its blood side or its hydraulic fluid side.

$PO_{2V}$ and $PO_{2A}$: by specific sensors, one (34) placed in the right heart ($PO_{2V}$), or else in the veins, and the other (36) in the aorta flow passing through the pump ($PO_{2A}$). The desired parameter is $PO_{2A}-PO_{2V}$. The system could be made to operate on the basis of using $PO_{2V}$ only, but that would reduce its performance.

F: by means of an electrocardiogram (ECG) or directly from the substitute frequency synthesizer, where appropriate. The ECG is picked up by a ventricular endocavity electrode 38 in the right heart. It defines the instant at which the right ventricle is depolarized from which it is possible to deduce the instant at which the left ventricle is depolarized, and the heartbeat frequency F. In a variant, the ECG can be picked up by an epicardiac electrode placed on the left ventricle.

dP/dt: this parameter is the mean slope of the pressure in the left ventricle during its isovolumetric contraction, which slope is obtained from the pressure difference and the duration between the beginning of depolarization and the opening of the aortic valve, as detected by the corresponding discontinuity in P(t).

Depending on the use that is to be made of it, data is deduced, after validation, from the measurements performed:

a) during the preceding heart cycle in order to track quickly or to estimate a trend; or b) on the basis of a sliding weighted mean over a determined number of preceding cycles, so as to perform smoothing and/or allow effects to stabilize.

The aortic pressure P(t) is sampled at predetermined intervals.

The data varies as a function of state parameters such as physical, gastrointestinal, or cerebral activity, posture, the environment, or the result of coexisting pathologies, drug levels, etc. The data is also to some extend interdependent.

EXPRESSION OF THE NEED OF THE HEART FOR ASSISTANCE

The need of the heart for assistance is determined from a set of data and combinations of reference data. This data set is established taking account of the cardiovascular pathology and is input into the appliance by programming.

The reference set has its own dynamics as a function of the state parameters: for example, the expression for normality when providing an effort is represented by the values for P(t), $PO_{2A}-PO_{2V}$, and dP/dt which are different from the values that represent normality at rest. The same applies to normality with varying levels of pharmaceuticals, etc.

The reference set must therefore be programmed at two levels:

one relating to reference data at rest; and another relating to algorithms for correcting the preceding data as a function of variations that are the result of daily activity. In this respect, the main factor giving rise to variation is physical activity, so the algorithms can generally be limited to representing physical activity by way of heartbeat frequency.

Finally, the reference data set is determined by two-variable data: P(t,F), $PO_{2A}(F)-PO_{2V}(F)$, F, dP/dt(F) and/or combinations of these data items.

In the event of a change in pharmaceutical levels or in pathological state, both levels of the programming should be modified accordingly.

Once programming has been performed, the differences observed in daily life relative to the reference values, once they have exceeded a certain threshold, determine the heart's need for assistance. For example, when providing an effort, any increase in $PO_{2A}-PO_{2V}$, or any drop in $PO_{2V}$, will trigger heart assistance which was not previously required while at rest, or which was required but to a lesser extent.

HEART ASSISTANCE

The way in which assistance is provided is defined by programming as a function of the nature, the amplitude, and the rate at which the differences vary.

As soon as assistance is provided, a tracking program is launched in addition to the above, e.g. including a higher rate of sampling, starting algorithms, tracking algorithms, terminating algorithms, etc., acting on the way in which assistance is delivered as a function of the way in which the disturbance causing it varies and as a function of the way in which the response of the organism varies.

WAYS IN WHICH ASSISTANCE IS GIVEN TO THE HEART

The assistance to be given to the heart is determined by piston displacement speeds u(t) during systole and v(t) during diastole, which correspond respectively to the volumes $\Sigma \cdot u(t)$ and $\Sigma \cdot v(t)$ that are respectively accumulated by and restored by the pump, and on the time of origin for said functions relative to the heart cycle, $t_A$ for u(t) and $t_R$ for v(t).

Determining u(t) and $t_A$

As explained above, the artificial increase in the aortic volume $\Sigma \cdot u(t)$ gives rise to an increase in the systolic flow rate which has repercussions on the energy delivered by the left ventricle and on the energy efficiency thereof. The effects are as beneficial as those of softening the arteries. It is also important for u(t) and $t_A$ to be properly matched to heart function.

For example, a preferred form of the profile for u(t) may decrease exponentially, by analogy with the elastic behavior of the arteries, while $t_A$ can control the beginning of systole by anticipation so as to reduce systolic pressure.

In practice, $t_A$ and the profile of u(t) are adjusted as a function of the patient by programming and they do not vary as a function of patient activity. The amplitude of u(t), and consequently of $\int_s u(t)dt$ constitutes the essential action parameter for giving assistance to the heart by artificially increasing aortic volume, or in other words, by decreasing postcharge on the left ventricle.

The amplitude of u(t), and in particular the corresponding quantity $\int_s u(t)dt$ for the total volume stored by the pump $\Sigma \cdot \int_s u(t)dt$, is determined as a function of the desired heart flow rate. Given the response time of the cardiovascular system to the impulse applied thereto, the amplitude u(t) can be incremented progressively, with each increment being defined as a function of the result of the preceding increment within a given time period, and is limited by the capacity of the heart and of the prosthesis to respond.

Determining v(t) and $t_R$

Reinjection is governed by the profile of v(t) and by $t_R$, with the amplitude of v(t) being dependent on the amplitude of u(t) since $\int_s u(t)dt = \int_D v(t)dt$, given that the piston returns to the same position after performing one cycle.

On the basis of arterial pressure at the beginning of diastole and in co-operation with arterial compliance, v(t) and $t_R$ determine the instantaneous arterial pressure and arterial flow rate during diastole. At equilibrium, total arterial flow rate during diastole, plus the arterial flow rate during systole, is naturally equal to the flow rate through the left ventricle.

When the state of the patient is stable, applying assistance to the heart associated with determined values of u(t), $t_A$, v(t), $t_R$ thus gives rise to a disturbance followed by a spontaneous re-equilibrium of the cardiovascular system to achieve a new operating regime defined by the heart flow rate, the various ventricular and aortic, systolic and diastolic pressures, and consequently the amounts of energy delivered by the heart and by the prosthesis.

It will be understood that:
  although giving assistance to the heart improves the cardiovascular state, the exact effects thereof are not known until after the state has stabilized, when it can be found by reading all of the data;
  assistance should preferably be applied to the heart by successive approximations; and
  assistance can be given to the heart at different degrees of intensity depending on the amount by which postcharge is to be diminished and on the energy supplied by the prosthesis.

PROGRAMMING PROTOCOL

Heart assistance can be either predetermined or else automatic.

Predetermined assistance is obtained by programming u(t), $t_A$, v(t), $t_R$ at rest and by the algorithm for correcting u(t) and the profile of v(t) and also $t_R$ as a function of the heartbeat frequency F.

Automatic assistance is obtained by programming the reference set, the correction algorithms for said set as a function of the state parameters, which, in practice, reduce to the heartbeat frequency F, the threshold for triggering assistance, and the intensity thereof.

Programming comprises the following operations:

A. For predetermined assistance:
  1. Implementing sensors; reading results.
  2. Programming assistance: u(t), $t_A$, v(t), $t_R$.
  3. Programming algorithms for correcting u(t), the profile of v(t), and $t_R$ as a function of heartbeat frequency.

B. For automatic assistance:
  1. Implementing sensors; reading results.
  2. Programming the reference set and the correction algorithms.
  3. Programming implementation of assistance as a function of differences (threshold and intensity) relative to the reference set.

OPERATION

The programmed appliance performs the following operations:
  1. Reading the sensors, and generating the data set in real time.
  2. Correcting the reference set in real time (automatic assistance).
  3. Determining the differences between the data set (1) and the reference set (2) (automatic assistance).
  4. Triggering assistance as a function of the differences (automatic assistance) or correcting assistance as a function of the heartbeat frequency (predetermined assistance).
  5. Triggering the tracking program. Protocol for successive approximations (automatic assistance).
  6. Holter registration of the data and of significant events, of operating parameters, in particular energy consumption.
  7. Recording statistical data.

It will be observed that the appliance can equally well correct the reference set (operation 2) or the data set in real time (inverse correction).

A COMPARATIVE EXAMPLE FOR THE RESULTING PRESSURE WAVE

FIG. 3 shows the shape of the pressure wave, i.e. the function P(t), for aortic pressure as a function of time.

Pressure is given in millimeters of mercury, which is the non-SI unit in which blood pressures are universally expressed in practice (1 mmHg=133.322 Pa).

The solid line curve shows aortic pressure without ventricular assistance, while the dashed line curve shows the same pressure with ventricular assistance, with reinjection (reduction of the variable volume 20) taking place between t=200 ms (end of systole) and t=340 ms.

Initially considering the curve for pressure without giving assistance to the heart, at equilibrium the pressure at the end of diastole is equal to the pressure at the beginning of systole, with the cycle being stabilized and repetitive.

The area defined by the curve of P(t) from t=0 to t=750 ms (one full cycle at a rate of 80 heart beats per minute) and the horizontal axis (going down to P=20 mmHg which is the end-of-diastole pressure of the left ventricle) is representative of the total capillary flow rate, equal to the total flow rate of the heart:

$$Q_{cardiac} = \text{area}(P)/R = 1/R \int_0^{750} P(t)dt$$

where R is the resistance of the arterial-venous capillaries, which is included in the relationship $Q_c = P/R$ giving the capillary flow rate.

With reference now to the curve for assistance being given to the heart (dashed line curve), various observations can be made.

Firstly, although reinjection takes place in the example shown at the beginning of diastole, it could equally well begin a little before the end of systole, providing it always comes to an end at t=340 ms. After the end of reinjection, the aorta, which has been dilatated by the reinjection, begins to discharge in approximately exponential manner into the downstream arterial network. As a result, the diastolic pressure at the end of diastole is greater than said pressure at the end of the preceding diastole. At the moment that assistance is put into operation, the cycle will therefore not be in equilibrium, and it will return to equilibrium a few cycles later.

Secondly, it can be observed that the difference between the solid line curve and the dashed line curve is representative of the difference in capillary flow rate with and without assistance.

With assistance, the capillary flow rate is lower during systole and greater during diastole. The balance (the difference between the area defined by the curves before and after the instant of reinjection) represents the contribution due to assisting the heart flow rate. The exact gain in heart flow rate can be determined after the pressure profile has stabilized, so as to take account of the fact that putting assistance into operation changes several physiological magnitudes such as diastolic and systolic pressure, filling of the left ventricle, energy of the right ventricle, resistance R (which decreases), frequency F (which decreases), etc. in particular with improved irrigation of the coronaries. Stabilization on a new equilibrium state will therefore not take place immediately.

It can also be observed that the heart flow rate, as represented by the area defined by the curve during the duration of a cycle, is delivered via the left ventricle during systole. That is to say that the area relating to systole represents the capillary flow rate during systole, while the heart flow rate stored by expansion of the artery during systole is represented by the area relating to diastole.

The pressure profile thus provides information immediately on the fraction of systolic ejection which is stored in the artery, and in the variable volume of the pump if the pump is active, and the fraction which is perfused directly into the downstream arterial network (or into the capillaries, ignoring any expansion of arteries downstream).

I claim:

1. A circuit (26) for controlling an implantable heart-assist pump (10) of the back-pressure balloon type, which pump comprises variable volume means (24) cooperating with a variable volume (20) through which blood flows for the purpose of modifying said variable volume (20) cyclically and in controlled manner, the circuit being characterized in that it includes (i) heart-assist control means for controlling the variable volume means and cooperating with (ii) means for sensing data representative of the state of the cardiovascular system, said sensing means comprising at least one means selected from the group consisting of:

means for sensing data representative of aortic pressure (P(t));

means for sensing data representative of venous oxygen concentration ($PO_{2V}$);

means for sensing data representative of aortic oxygen concentration ($PO_{2A}$);

means for sensing data representative of heartbeat frequency (F); and means for sensing data representative of the myocardial contractility (dP/dt).

2. The circuit of claim 1, wherein the heart-assist control means includes at least one of the means selected from the group consisting of:

means for controlling the rate of variation (u(t)) of said variable volume during systolic phase of myocardium;

means for controlling the rate of variation (v(t)) of said variable volume during diastolic phase of the myocardium;

means for controlling the instant ($t_A$) at which said variable volume variation starts during the systolic phase; and means for controlling the instant ($t_R$) at which said variable volume variation starts during the diastolic phase.

3. The circuit of claim 2, in which operation of the heart-assist control means is predetermined on the basis of a programmed appliance:

(i) programmed with a set of rest values for at least one reference parameter selected from the group consisting of: the rate (u(t)) at which the volume varies during the systolic phase of the myocardium; the rate (v(t)) at which the volume varies during the diastolic phase of the myocardium; the instant ($t_A$) at which said volume variation during the systolic phase begins; and the instant ($t_R$) at which said volume variation during the diastolic phase begins; and (ii) programmed with an algorithm for correcting at the least one reference parameter as a function of the heartbeat frequency (F).

4. The circuit of claim 2, further including means for sensing data (MV), representative of the metabolic needs of the patient, cooperating with said heart-assist control means.

5. The circuit of claim 4, in which operation of the heart-assist control means is automatic on the basis of:

(i) said means for sensing data sensing a representative data set generated in real time comprising at least sensed parameters of: aortic pressure (P(t)); venous oxygen concentration ($PO_{2V}$); aortic oxygen concentration ($PO_{2A}$); heartbeat frequency (F); and myocardial contractility (dP/dt);

(ii) a programmed appliance programmed with a set of reference parameters corresponding to said sensed parameters;

(iii) differences determined between said representative data set and said reference parameters set; and (iv) an algorithm programmed on said programmed device for implementing the variable volume means as a function of said differences determined; in which the algorithm for implementing the variable volume means serves to track heart assistance.

6. The circuit of claim 5, in which said algorithm serves to track heart assistance by applying the assistance by successive approximations.

7. The circuit of claim 2, further including means for sensing data (G), representative of the physical activity of the patient, cooperating with said heart-assist control means.

8. The circuit of claim 7, in which operation of the heart-assist control means is automatic on the basis of:

(i) said means for sensing data sensing a representative data set generated in real time comprising at least sensed parameters of: aortic pressure (P(t)); venous oxygen concentration ($PO_{2V}$); aortic oxygen concentration ($PO_{2A}$; heartbeat frequency (F); and myocardial contractility (dP/dt);

(ii) a programmed appliance programmed with a set of reference parameters corresponding to said sensed parameters;

(iii) differences determined between said representative data set and said reference parameters set; and (iv) an algorithm programmed on said programmed device for implementing the variable volume means as a function of said differences determined; in which the algorithm for implementing the variable volume means serves to track heart assistance.

9. The circuit of claim 8, in which said algorithm serves to track heart assistance by applying the assistance by successive approximations.

10. The circuit of claim 2, in which operation of the heart-assist control means is automatic on the basis of:

(i) said means for sensing data sensing a representative data set generated in real time comprising at least sensed parameters of: aortic pressure (P(t)); venous oxygen concentration ($PO_{2V}$); aortic oxygen concentration ($PO_{2A}$); heartbeat frequency (F); and myocardial contractility (dP/dt);

(ii) a programmed appliance programmed with a set of reference parameters corresponding to said sensed parameters;

(iii) differences determined between said representative data set and said reference parameters set; and (iv) an algorithm programmed on said programmed device for implementing the variable volume means as a function of said differences determined.

11. The circuit of claim 10, in which the algorithm for implementing the variable volume means serves to track heart assistance.

12. The circuit of claim 11, in which said algorithm serves to track heart assistance by applying the assistance by successive approximations.

* * * * *